United States Patent

Datta et al.

[11] Patent Number: 6,159,881
[45] Date of Patent: *Dec. 12, 2000

[54] THERMOFORMABLE BARRIER NONWOVEN LAMINATE

[75] Inventors: Paul Joseph Datta, Appleton, Wis.; Stanley Michael Gryskiewicz, Woodstock; Richard Daniel Pike, Norcross, both of Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/808,326

[22] Filed: Feb. 28, 1997

Related U.S. Application Data

[63] Continuation of application No. 08/445,149, May 19, 1995, Pat. No. 5,695,376, which is a continuation of application No. 08/303,786, Sep. 9, 1994, abandoned.

[51] Int. Cl.⁷ .................................................. A61F 13/00
[52] U.S. Cl. ......................... 442/409; 442/353; 442/411
[58] Field of Search .................................. 442/409, 411, 442/353

[56] References Cited

U.S. PATENT DOCUMENTS

| | | | |
|---|---|---|---|
| Re. 30,955 | 6/1982 | Stanistreet | 156/308 |
| 2,104,423 | 1/1938 | Hughes | 128/290 |
| 2,778,405 | 1/1957 | Stephens et al. | 154/28 |
| 2,949,646 | 8/1960 | Clark | 19/155 |
| 2,964,039 | 12/1960 | Johnson, Jr. et al. | 128/290 |
| 3,015,598 | 1/1962 | Jones | 156/222 |
| 3,023,839 | 3/1962 | Best | 183/49 |
| 3,106,207 | 10/1963 | Dudley | 128/290 |
| 3,318,748 | 5/1967 | Hurst | 156/224 |
| 3,423,266 | 1/1969 | Davies et al. | 156/167 |
| 3,511,747 | 5/1970 | Davies | 161/150 |
| 3,523,149 | 8/1970 | Hartmann | 264/90 |
| 3,589,956 | 6/1971 | Kranz et al. | 156/62.4 |
| 3,595,731 | 7/1971 | Davies et al. | 161/150 |
| 3,607,500 | 9/1971 | Field | 264/119 |
| 3,616,002 | 10/1971 | Paquette et al. | 156/180 |
| 3,692,618 | 9/1972 | Dorschner et al. | 161/72 |
| 3,730,662 | 5/1973 | Nunning | 425/131 |
| 3,766,922 | 10/1973 | Krusko | 128/284 |
| 3,802,817 | 4/1974 | Matsuki et al. | 425/66 |
| 3,805,790 | 4/1974 | Kaczmarzky et al. | 127/290 |
| 3,847,729 | 11/1974 | Hartmann | 161/256 |
| 3,957,558 | 5/1976 | Lee et al. | 156/212 |
| 4,068,036 | 1/1978 | Stanistreet | 428/296 |

(List continued on next page.)

FOREIGN PATENT DOCUMENTS

| | | | |
|---|---|---|---|
| 0 124 387 | 11/1984 | European Pat. Off. | B29D 3/02 |
| 0 249 261 | 12/1987 | European Pat. Off. | D04H 1/00 |
| 0 291 189 | 11/1988 | European Pat. Off. | D04H 1/00 |
| 0 337 597 | 10/1989 | European Pat. Off. | D04H 1/06 |
| 0 439 962 | 8/1991 | European Pat. Off. | A61F 13/15 |
| 0518340A1 | 6/1992 | European Pat. Off. . | |
| 0 511 025 | 10/1992 | European Pat. Off. | D04H 1/00 |
| 0 532 035 | 3/1993 | European Pat. Off. | A61F 13/15 |
| 0 586 924 | 3/1994 | European Pat. Off. | D04H 1/54 |
| 0139484B1 | 9/1994 | European Pat. Off. . | |
| 0 241 221 | 4/1997 | European Pat. Off. . | |
| 3007343 | 9/1981 | Germany . | |
| 1089414 | 11/1967 | United Kingdom . | |
| WO 88/04194 | 6/1988 | WIPO | B01D 46/24 |
| 91/16870 | 11/1991 | WIPO . | |
| 93/16666 | 9/1993 | WIPO | A61F 5/44 |

*Primary Examiner*—Jenna Davis

[57] ABSTRACT

The present invention provides a barrier laminate having a barrier layer and a lofty crimped-fiber nonwoven web layer, which laminate provides a foam-like resiliency, cloth-like texture and liquid barrier property. The barrier layer of the laminate is selected from films, microfiber nonwoven webs and laminates thereof, and the crimped-fiber web layer, which contains a structural fiber component and an heat-activatable adhesive component, has substantially uniformly distributed interfiber bonds. Additionally provided are thermoformed articles from the laminate and a thermoforming process for producing the articles.

20 Claims, 2 Drawing Sheets

U.S. PATENT DOCUMENTS

| | | | |
|---|---|---|---|
| 4,195,112 | 3/1980 | Sheard et al. | 428/288 |
| 4,297,408 | 10/1981 | Stead et al. | 428/420 |
| 4,340,563 | 7/1982 | Appel et al. | 264/518 |
| 4,372,098 | 2/1983 | Mason | 53/412 |
| 4,392,903 | 7/1983 | Endo et al. | 156/167 |
| 4,397,644 | 8/1983 | Matthews et al. | 604/378 |
| 4,405,326 | 9/1983 | Lenaghar | 604/385 |
| 4,536,440 | 8/1985 | Berg | 428/284 |
| 4,547,420 | 10/1985 | Krueger et al. | 428/229 |
| 4,663,220 | 5/1987 | Wisneski et al. | 428/221 |
| 4,666,647 | 5/1987 | Enloe et al. | 264/121 |
| 4,678,527 | 7/1987 | Ulman | 156/213 |
| 4,701,177 | 10/1987 | Ellis | 604/385 |
| 4,729,371 | 3/1988 | Krueger et al. | 128/206 |
| 4,741,941 | 5/1988 | Englebert et al. | 428/71 |
| 4,744,848 | 5/1988 | Andrews et al. | 156/224 |
| 4,770,657 | 9/1988 | Ellis et al. | 604/385 |
| 4,786,351 | 11/1988 | Elliottot et al. | 156/245 |
| 4,795,668 | 1/1989 | Krueger et al. | 428/174 |
| 4,807,619 | 2/1989 | Dyrud et al. | 128/206.16 |
| 4,830,904 | 5/1989 | Gessner et al. | 428/219 |
| 4,833,862 | 5/1989 | Bortolani et al. | 53/427 |
| 5,064,492 | 11/1991 | Friesch | 156/191 |
| 5,080,742 | 1/1992 | Takahashi | 156/212 |
| 5,082,720 | 1/1992 | Hayes . | |
| 5,141,805 | 8/1992 | Nohara et al. . | |
| 5,143,779 | 9/1992 | Newkirk et al. | 428/218 |
| 5,164,254 | 11/1992 | Todd et al. | 428/290 |
| 5,171,302 | 12/1992 | Buell | 604/385 |
| 5,225,014 | 7/1993 | Ogata et al. | 156/73.2 |
| 5,271,997 | 12/1993 | Baigas, Jr. . | |
| 5,298,321 | 3/1994 | Isoda et al. . | |
| 5,307,796 | 5/1994 | Kronzer et al. | 128/206.16 |
| 5,399,174 | 3/1995 | Yeo | 604/365 |
| 5,575,874 | 11/1996 | Griesbach, III et al. | 156/167 |
| 5,597,645 | 1/1997 | Pike et al. | 96/99 |
| 5,643,653 | 7/1997 | Griesbach, III et al. | 428/120 |
| 5,714,107 | 2/1998 | Levy et al. | 264/289.3 |

FIG. 3

THERMOFORMABLE BARRIER NONWOVEN LAMINATE

This application is a continuation of application Ser. No. 08/445,149 entitled "Thermoformable Barrier Nonwoven Laminate" and filed in the U.S. Patent and Trademark Office on May 19, 1995 now U.S. Pat. No. 5,695,376 which is a continuation of Ser. No. 08/303,786, filed Sep. 9, 1994, now abandoned. The entirety of this application is hereby incorporated by reference.

BACKGROUND OF THE INVENTION

The present invention is related to a thermoformable nonwoven laminate of a nonwoven web layer and a barrier layer, which has cloth-like appearance and texture as well as high resiliency.

Absorbent personal-care articles such as sanitary napkins, disposable diapers, incontinent-care pads and the like are being used widely, and much effort has been made to improve efficiencies and functionalities of these articles. Thick, flat personal-care articles of the past design that do not fit the shape of the human body and do not conform to the movements of the user are largely replaced by resiliently conforming three-dimensional, body-shaped articles.

The outer-cover of these shaped personal-care articles needs to prevent collected liquid in the article from permeating to the outside, and in addition, it needs to be flexibly conformable to the movements of the user. Consequently, the covers are typically produced from a flexible and liquid impermeable material, e.g., a flexible thermoplastic film. In general, these flexible cover materials are formed into three-dimensional articles by gathering portions of the flexible material to form a basin-like or an hour glass-like shape that conforms to the body contour of the user. Suggestions have been made in the art that improved variants of the outer-cover can be produced from a laminate of a thin film and a thin nonwoven web to add desirable textural properties to the cover. For example, U.S. Pat. No. 4,701,177 discloses a feminine pad having a laminate outer-cover of a film and a nonwoven web. The shape of the gathered basin typically is retained by attaching elastic strips to hold the gathers in position and to provide a limited resiliency to the shaped article. However, the articles produced from the film and film laminate may not be highly suitable for certain applications where the articles need to provide a high degree of resiliency since the film or film laminate does not have high physical strength and the elastic strips only provide a limited resiliency and conformability to the movements of the user.

Alternatively, the outer-cover of shaped personal-care articles is produced from a flexible polyurethane or polyethylene foam sheet, which provides desirable resiliency and liquid-barrier properties. A foam sheet is molded or thermoformed into a self-supporting basin, eliminating the use of the elastic strips and providing improved resiliency and conformability. These thermoformed resilient articles tend to conform to the user's movements and retain their original shape after the articles are subjected to deforming pressures, improving efficacy and functionality of the articles. However, the articles thermoformed from these foam sheets are often characterized as having a rubbery or plastic-like texture.

There still is a need for thermoformable structures and thermoformed articles therefrom that exhibit a foam-like resiliency and a cloth-like texture. In addition, there is a need for a thermoforming process that thermoforms the thermoformable structures without appreciably diminishing the desirable resiliency and surface properties of the structures.

SUMMARY OF THE INVENTION

The present invention provides a barrier laminate having a barrier layer and a lofty crimped-fiber nonwoven web layer, which laminate provides a foam-like resiliency, cloth-like texture and liquid barrier property. The barrier layer of the laminate is selected from films, microfiber nonwoven webs and laminates thereof, and the crimped-fiber web layer, which contains a structural fiber component and an heat-activatable adhesive component, has substantially uniformly distributed interfiber bonds.

Additionally provided are three-dimensional thermoformed article that exhibits a foam-like resiliency, cloth-like texture and liquid barrier property, and is thermoformed from the barrier laminate; and a process for thermoforming the laminate, which contains the steps of heating the laminate to melt the adhesive component of the nonwoven fiber web and to make the nonwoven fiber web pliable without melting said structural fiber component, shaping the pliable web on a mold by lightly applying a guiding pressure, and cooling the shaped laminate to solidify the melted adhesive component and to form interfiber bonds, wherein the thermoformed article has a density-over-area ratio between about 1 and about 2.5. The present invention also provides a personal care article containing a thermoformed liquid-barrier shell, a liquid-absorbent core and a liquid-permeable liner, wherein the shell is thermoformed from the barrier laminate.

The present barrier laminate can be thermoformed to provide resilient, cloth-like three-dimensional articles, for example, personal-care articles, automotive interior parts, cloth linings and the like.

DETAILED DESCRIPTION OF THE INVENTION

Figure 1:
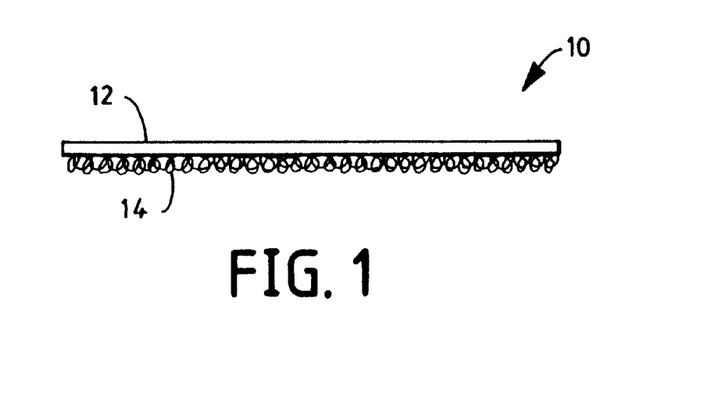
FIG. 1 illustrates an exemplary barrier laminate of the present invention.

There is provided in accordance with the present invention a thermoformable liquid-barrier laminate having a cloth-like texture and a foam-like resiliency. Additionally provided are thermoformed articles made from the laminate. As illustrated in FIG. 1, the liquid-barrier laminate 10 has a liquid-barrier layer 12 and a lofty nonwoven fiber web layer 14 which has substantially uniformly distributed interfiber bonds throughout. The lofty nonwoven laminate is highly suitable for producing thermoformed articles having a cloth-like texture and a foam-like compression resiliency. The term "foam-like" as used herein indicates flexible foam-like, such as flexible polyurethane foam-like, properties which can be characterized as resiliently reversible deformability and limited resistance to an applied load. Illustrative thermoformed articles that can be produced from the laminate include thermoformed personal-care articles and components thereof, such as body-conforming sanitary napkin shells, shape-retaining diaper components, incontinent care product components and the like.

Figure 2:
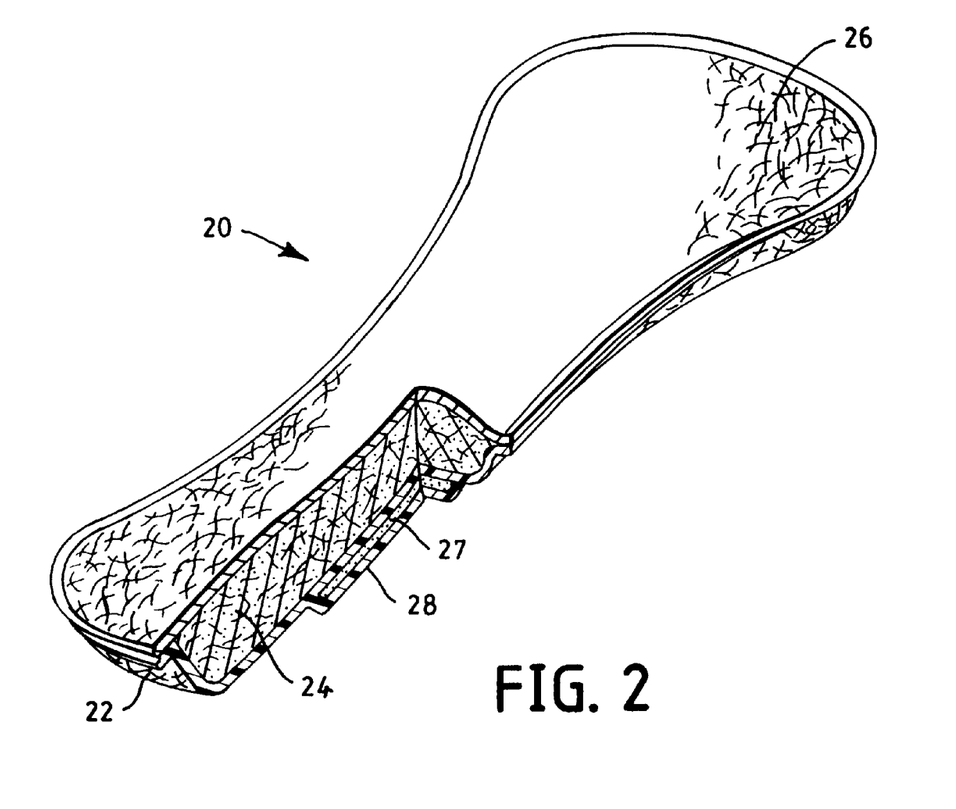
FIG. 2 illustrates a sanitary pad containing a thermoformed article of the present invention.

For illustration purposes, the present invention is described hereinafter in reference to a shaped sanitary pad. The term "sanitary pad" as used herein indicates a menstrual or an incontinence pad. As illustrated in FIG. 2, a thermoformed hourglass shaped sanitary pad 20 has a liquid-barrier outer shell 22, an absorbent core 24 and a liquid-permeable liner 26. The pad is also provided with a strip of a pressure sensitive adhesive 27 and a removable peel strip 28 covering the adhesive strip. The peel strip 28 may be removed to expose the adhesive for attachment to an undergarment.

The outer shell 22 is thermoformed from a liquid-barrier laminate of the present invention into a body-conforming basin with its nonwoven layer exposed to the outside such that the user's skin contacts the nonwoven surface. The nonwoven layer of the outer shell 22 provides a soft, cloth-like texture to promote the comfort of the user while the liquid-barrier layer prevents absorbed liquids from permeating to the nonwoven side of the shell 22. The liquid-permeable liner 26, which covers the opening of the shell 22 and retains the absorbent core 24 in the shell 22, is sealed to the shell 22, for example, adhesively, thermally, or ultrasonically. The absorbent core 24 may be any absorbent material that will absorb bodily exudates, such as catamenial fluids and urine. Suitable absorbent materials include wood pulp fluff, rayon fiber fluff, cotton, multi-layered cellulose wadding and combinations thereof. The absorbent core may also contain a natural or synthetic superabsorbent material, e.g., polyacrylamides, polyarylic acids, metal salts of polyacrylic acid, polyacrylates, polymers and copolymers of vinyl sulfonic acid, polyacrylate grafted starches, polyvinyl ethers, polyvinylpyrrolidone, sulfonated polystyrene polysulfoethyl acrylate, and the like. Particularly suitable absorbent cores and their structures are disclosed in U.S. Pat. No. 5,147,343 to Kellenberger, which is herein incorporated by reference. Additionally, the absorbent core may be a coformed absorbent material. A coformed material is described in U.S. Pat. No. 4,100,324, which is herein incorporated by reference. This absorbent material has a fabric-like finish and is made up of an air-formed matrix of thermoplastic fibers, particularly meltblown fibers, with absorbent pulp fibers dispersed throughout the matrix.

The liquid-permeable liner 26 may be any suitable liquid-permeable material that allows rapid movement of liquid away from its source to the absorbent core 24. Typical of such materials are nonwoven webs, perforated films and composites of these materials. Particularly suitable liquid-permeable liners are disclosed in U.S. Pat. No. 4,397,644 to Matthews et al.

As stated above, the outer shell 22 is thermoformed from a laminate of a lofty nonwoven web layer and a liquid-barrier layer. The nonwoven web layer of the thermoformed articles of the present invention is thermoformed in such a way, as further discussed below, to avoid significant compaction of the lofty structure of the nonwoven layer and to avoid damaging the liquid-barrier layer. The combination of the lofty structure and the uniformly distributed interfiber bonds of the nonwoven layer provides physical strength and resiliency as well as cloth-like, soft textural properties to the thermoformed article.

The cloth-like, soft textural properties of the thermoformed shell 22 is highly significant for the comfort of the user. The wall of the shell generally extends up into the crease between the legs and the pudendum of the user, and therefore, the outer wall portions may come in contact with the legs of the user. Consequently, the outer wall portion should provide comfortable nonirritating textural properties.

The liquid-barrier layer of the present invention is fabricated from a liquid-barrier material, such as a film or microfiber nonwoven web that provides a high liquid-barrier property. The term "liquid-barrier layer" as used herein denotes a layer of a material that is either impervious to both liquid and gas, or relatively impervious to liquids and yet may be pervious to air and/or liquid vapors, particularly to water vapor. The liquid-barrier layer may be characterized as having a hydrostatic head of at least about 50 cm, preferably at least about 70 cm, as measured in accordance with the standard hydrostatic pressure test AATCCTM No. 127-1977.

Suitable materials for the liquid-barrier layer include thermoplastic films having a thickness between about 0.1 mil and about 100 mil, desirably between about 0.5 mil and about 10 mil. Suitable films desirably are not highly oriented or do not contain high molecular stress in order to prevent high shrinkages of the barrier layer during the thermoforming process. Suitable films can be produced by any known film forming process, e.g., an extrusion-casting, a meltblowing or calendering process, and formed from any water-insoluble thermoplastic polymer that is known to form films, including, but not limited to, polyolefins, e.g., polyethylene, polypropylene, polybutylene and the like; polyamides, e.g., nylon 6, nylon 6/6, nylon 10, nylon 12 and the like; polyesters, e.g., polyethylene terephthalate, polybutylene terephthalate and the like; polycarbonates; polystyrenes; thermoplastic elastomers, e.g., ethylene-propylene rubbers, styrenic block copolymers and the like; vinyl polymers; polyurethane; acrylonitrile copolymers and blends and copolymers thereof. Particularly suitable polymers for the present invention are polyolefins, including polyethylene, e.g., linear low density polyethylene, low density polyethylene, medium density polyethylene, high density polyethylene and blends thereof; polypropylene, e.g., isotactic polypropylene, syndiotactic polypropylene, blends thereof, and blends of one or more of these polypropylenes and atactic polypropylene; polybutylene; and copolymers as well as blends thereof. The polymer compositions forming the films may also contain additives for lowering the bonding temperature and for enhancing the abrasion resistance, strength, adhesiveness and softness of the films.

Suitable liquid-barrier films may contain micro-perforations or pores that allow the films to breath, i.e., the films are permeable to air and vapors but are highly resistant to permeation of liquids and particulates. Such breathability of the fluid barrier layer promotes the comfort of the user, especially when the thermoformed articles are utilized in skin-contacting applications. Suitable microporous films are well known in the art and, for example, disclosed in U.S. Pat. No. 4,347,844 to Ohki et al.

Additionally suitable liquid-barrier layer materials are microfiber nonwoven webs having a high hydrostatic head value. Useful microfiber nonwoven webs include meltblown fiber webs having a high hydrostatic head value as specified above. The term "meltblown fibers" as used herein indicates fibers formed by extruding a molten thermoplastic polymer through a plurality of fine, usually circular, die capillaries as molten threads or filaments into converging high velocity gas streams which attenuate the filaments of molten thermoplastic polymer to reduce their diameter. In general, meltblown fibers have an average fiber diameter of up to about 10 $\mu$m. After the fibers are formed and before the fibers are fully solidified, they are carried by the high velocity gas stream and deposited on a collecting surface to form a relatively compacted, autogenously bonded web of randomly disbursed meltblown fibers.

The lofty nonwoven web layer of the present invention that has substantially uniformly distributed interfiber bonds contains a structural fiber component and a heat-activatable adhesive component. The adhesive component may be added as an external adhesive or may form a portion of the fibers of the nonwoven web, as further discussed below. Suitable fibers for the present invention are crimped fibers including crimped homocomponent fibers (i.e., the fibers are fabricated from a homogeneous polymer composition) and crimped multicomponent conjugate fibers (i.e., the fibers contain at least two component polymer compositions which occupy distinct cross sections along substantially the entire length of the fibers). Particularly suitable are crimped conjugate spunbond or staple fibers, and most suitable conjugate fibers for the present nonwoven web are bicomponent conjugate fibers. Of the suitable fibers, multicomponent conjugate fibers having component polymers that have different melting points are particularly desirable for the present invention in that no additional and extraneous adhesive component needs to be introduced to bond the nonwoven web, simplifying the nonwoven web manufacturing process.

The crimp level of the fibers may be changed to provide different properties to the web, including different density, strength, softness and texture. In general, highly crimped fibers bonded in accordance with the present invention provide a lofty, soft web. Suitable fibers for the present nonwoven web have at least about 2 crimps per extended inch, desirably between about 2 and about 50 crimps per extended inch, more desirably between about 3 and about 30 crimps per extended inch, as measured in accordance with ASTM D-3937-82. Suitable spunbond fibers and staple fibers for the present invention have an average diameter from about 5 $\mu$m to about 100 $\mu$m, preferably from about 10 $\mu$m to about 50 $\mu$m.

The term "fibers" as used herein refers both to staple fibers and to filaments, which are continuous fibers. The term "spunbond fibers" refers to fibers formed by extruding molten thermoplastic polymers as filaments from a plurality of relatively fine, usually circular, capillaries of a spinneret, and then rapidly drawing the extruded filaments by an eductive or other well-known drawing mechanism to impart molecular orientation and physical strength to the filaments. The drawn fibers are deposited onto a collecting surface in a highly random manner to form a nonwoven web having essentially a uniform density, and then the nonwoven web is bonded to impart physical integrity and strength. The processes for producing spunbond fibers and webs therefrom are disclosed, for example, in U.S. Pat. Nos. 4,340,563 to Appel et al. and 3,692,618 to Dorschner et al. A particularly suitable conjugate spunbond fiber web production process is disclosed in commonly assigned U.S. patent application Ser. No. 08/933,444, filed Aug. 21, 1993, which is published as European Patent Application 0 586 925. The term "staple fibers" refers to non-continuous fibers. Staple fibers are produced with a conventional fiber spinning process and then cut to a staple length, from about 1 inch to about 8 inches. Such staple fibers are subsequently carded, wet-laid, or air-laid and then thermally bonded to form a nonwoven web.

Suitable crimped monocomponent spunbond fibers can be produced in accordance with any conventional spunbond fiber-forming process provided that the process is modified to have an in-situ crimping step in the fiber-spinning process. For example, during the fiber spinning process, the spun fibers exiting the spinneret are asymmetrically cooled across the cross-section to generate a solidification gradient within the cross-section of the fibers and thus to cause fibers to crimp, particularly in the form of helical crimps. Analogously, multicomponent conjugate spunbond fibers can also be produced with the above-described asymmetrical cooling process.

Suitable crimped monocomponent staple fibers for the present invention can be produced from strands of continuous filaments which are spun with any well known staple fiber spinning process and then crimped either with the above-described asymmetrical cooling process during the drawing and solidification step of the filament spinning process or with a known mechanical crimping process, e.g., a stuffer box or gear crimping process, after the strands of filaments are fully formed but before the strands are cut to staple lengths. Suitable crimped multicomponent conjugate staple fibers can be formed with the processes described above for monocomponent staple fibers by replacing its spinneret assembly with a conjugate fiber spinneret assembly, which is well known in the art and, for example, described in U.S. Pat. No. 3,730,662 to Nunning. Spun multicomponent conjugate filaments can also be crimped by mechanically drawing the filaments before they are cut to a staple length. Suitable crimped multicomponent conjugate fibers are commercially available from, for example, Chisso, Hoechst Celanese, Hercules and BASF.

Alternatively, crimped conjugate fibers, including spunbond fibers and staple fibers, can be fabricated from two or more component polymers that have different crystallization and/or solidification properties. Such conjugate fibers can be crimped during the solidification stage of the fiber spinning process since these differences in the component polymers create crystallization and/or solidification gradients, and therefore densification gradients in the fibers, which spontaneously cause crimps. Further, conjugate fibers containing component polymers of different crystallization properties possess "latent crimpability", which can be heat activated to impart crimps. The latent crimpability is imparted in the conjugate fibers due to incomplete crystallization of one or more of the slow crystallizing component polymers. When such conjugate fibers are heat treated to allow further crystallization of the slow crystallizing component polymers, the polymers further densify and shrink. The shrinkage disparity among the component polymers of the conjugate fibers during the heat treatment causes the fibers to crimp. An exemplary process for producing highly suitable conjugate fibers having such latent crimpability and nonwoven webs made therefrom is disclosed in aforementioned U.S. patent application Ser. No. 08/933,444, filed Aug. 21, 1993, which in its entirety is herein incorporated by reference.

Crimps in conjugate fibers that have the latent crimpability can be imparted during or after the fiber spinning step, or after the fibers are laid to form a nonwoven web when fibers having the latent crimpability are employed. However, it is highly desirable to fully impart crimps in the fibers before they are laid or deposited to form a nonwoven web to ensure dimensional stability and uniformity of the web since it is highly impractical to control the movement of the crimping fibers to protect against dimensional changes and to ensure the uniformity of the web.

Suitable fibers of the present invention are uniformly deposited onto a forming surface to form a loosely entangled nonwoven fiber web and then bonded to provide physical integrity and strength to the nonwoven web. As is known in the art, staple fibers are deposited on a forming surface with a conventional carding process, e.g., a woolen or cotton carding process, wet-laid, or air-laid; and spun, drawn spunbond fibers are directly deposited onto a forming surface. The deposited fiber web in accordance with the present invention is bonded with a bonding process that does not appreciably or significantly compact the web and provides substantially uniform interfiber bonds throughout the web.

As discussed above, the suitable nonwoven fiber webs may contain an external heat-activatable adhesive component, which may be in the form of a powder or liquid that is uniformly applied or sprayed, or of fibers that are intermixed with the web fibers. Adhesives particularly suitable for the present invention are conventional hot-melt adhesives, such as polyethylene-, polyamide-, polyester- and ethylene-vinyl acetate copolymer-based hot-melt adhesives, and the adhesives are selected to have a melting point below the melting point of the structural component of the nonwoven layer.

As a more desirable embodiment of the present invention, suitable nonwoven webs are produced from conjugate fibers containing component polymers that have different melting points such that the lower melting component polymer, the adhesive component, can be melted and thus rendered adhesive while allowing the higher melting component polymer, the structural component, to maintain the physical integrity and structure of the nonwoven web. The melted adhesive component polymer autogenously adheres to adjacent fibers, especially at the cross-over contact points. Consequently, the melting point difference between the adhesive component and the structural component is at least about 5° C., desirably at least about 10° C., more desirably at least about 25° C. In accordance with the present invention, suitable conjugate fibers should have the adhesive component polymer at least partially exposed to the surface along substantially the entire length of the fibers. Particularly suitable conjugate fibers should have from about 20% to about 80%, preferably from about 40% to about 60%, by weight of the adhesive polymer. For the present invention, desirable configurations for the conjugate fibers include side-by-side configurations and sheath-core configurations, and suitable sheath-core configurations include eccentric sheath-core and concentric sheath-core configurations. If a sheath-core configuration is employed, the adhesive polymer should form the sheath.

As stated above, the crimped-fiber nonwoven web of the present invention is bonded to have a lofty structure that contains interfiber bonds throughout the web. Bonding processes useful for the present invention should raise the temperature of the deposited nonwoven web to activate its adhesive component without applying significant compacting pressures on the web. The melted or activated adhesive component polymer forms substantially uniform interfiber bonds throughout the web, particularly at the fiber cross-over contact points, providing a lofty nonwoven web that is soft and yet strong and has a high level of resiliency. Unlike suitably bonded webs of the present invention that have substantially evenly distributed interfiber bonds, other conventional bonded nonwoven webs, for example, point bonded nonwoven webs, do not provide the necessary resiliency. Bonding processes particularly useful for the present invention include through-air bonding, hot-oven bonding and infrared-heater bonding processes; and more particularly useful bonding processes are through-air bonding processes. The duration and temperature of the bonding process can be varied to accommodate the temperature and speed limitations of the selected bonding equipment. However, it is important that the combination of duration and temperature of the bonding process is sufficiently long and high as to melt the adhesive component of the web but is not excessively long and high as to melt the structural component, preserving the physical and dimensional integrities and preventing shrinkage of the fiber webs. For example, when polypropylene and polyethylene are used as the component polymers for a conjugate-fiber nonwoven web and a through-air bonding process is used, the air flowing through the through-air bonder may have a temperature between about 230° F. and about 280° F. at a velocity from about 100 to about 500 feet per minute, and the dwell time of the web in the bonder is desirably less than about 6 seconds.

Monocomponent and conjugate fibers suitable for the present invention can be produced from a wide variety of thermoplastic polymers that are known to form fibers. Desirably, when conjugate fibers are utilized, the component polymers are selected in accordance with the above-described selection criteria including melting points and crystallization properties. Suitable polymers for the present invention include, but are not limited to, polyolefins, e.g., polyethylene, polypropylene, polybutylene and the like; polyamides, e.g., nylon 6, nylon 6/6, nylon 10, nylon 12 and the like; polyesters, e.g., polyethylene terephthalate, polybutylene terephthalate and the like; polycarbonates; polystyrenes; thermoplastic elastomers, e.g., ethylene-propylene rubbers, polyurethane, styrenic block copolymers, copolyester elastomers and polyamide elastomers and the like; fluoropolymers, e.g., polytetrafluoroethylene and polytrifluorochloroethylene; vinyl polymers, e.g., polyvinyl chloride; and blends and copolymers thereof. Particularly suitable polymers for the present invention are polyolefins, including polyethylene, e.g., linear low density polyethylene, low density polyethylene, medium density polyethylene, high density polyethylene and blends thereof; polypropylene; polybutylene; and copolymers as well as blends thereof. Of the suitable polymers, particularly suitable polymers for the high melting component of conjugate fibers include polypropylene, copolymers of polypropylene and ethylene and blends thereof, more particularly polypropylene, and particularly suitable polymers for the low melting component include polyethylenes, more particularly linear low density polyethylene, high density polyethylene and blends thereof. In addition, the polymer components may contain additives or thermoplastic elastomers for enhancing the crimpability and/or lowering the bonding temperature of the fibers, and enhancing the abrasion resistance, strength and softness of the resulting webs. For example, the low melting polymer component may contain about 5 to about 20% by weight of a thermoplastic elastomer such as an ABA' block copolymer of styrene, ethylene-butylene and styrene. Such copolymers are commercially available and some of which are identified in U.S. Pat. No. 4,663,220 to Wisneski et al. An example of highly suitable elastomeric block copolymers is KRATON G-2740. Another group of suitable additive polymers is ethylene alkyl acrylate copolymers, such as ethylene butyl acrylate, ethylene methyl acrylate and ethylene ethyl acrylate, and the suitable amount to produce the desired properties is from about 2 wt % to about 50 wt %, based on the total weight of the low melting polymer component. Yet other suitable additive polymers include polybutylene copolymers and ethylene-propylene copolymers.

Nonwoven webs suitable for the present invention typically have a density of about 0.01 to about 0.15 g/cm$^3$, preferably about 0.02 to about 0.1 g/cm$^3$, more preferably about 0.03 to about 0.07 g/cm$^3$ and a basis weight of about 0.3 to about 20 oz. per square yard (osy), preferably about 0.5 to about 15 osy, more preferably about 0.75 to about 10 osy.

In accordance with the present invention, the liquid-barrier layer and the nonwoven fiber web layer can be laminated with an adhesive. A variety of adhesives that are compatible with the component polymers of the two layers can be employed, which include conventional hot-melt adhesives, e.g., polyethylene-, polyamide-, polyester- and ethylene-vinyl acetate copolymer-based hot melt adhesives; latex adhesives; acrylate adhesives; silicone adhesives and the like. The suitable adhesives may be in a powder, liquid or film form. Of these suitable adhesives, particularly suitable adhesives are hot-melt adhesives since hot-melt adhesives can be melted to better accommodate the deforming movements of the liquid-barrier and nonwoven web layers during the thermoforming process. The two layers can be laminated with any film or nonwoven web laminating process known in the art. For example, a melted hot-melt adhesive may be sprayed on a film, and then the film is adjoined with a nonwoven fiber web before the hot-melt adhesive solidifies using a low-pressure nip rolls.

Alternatively, if at least one of the component polymers of the liquid-barrier layer or the nonwoven fiber web layer is selected from polymers that can be rendered adhesive when heated and then readily binds to the other layer, the two layers can be laminated during the thermoforming operation without using an external adhesive. The two layers are heated to activate the adhesive polymer component and to make the two layers pliable, and then the heated layers are placed and thermoformed in a mold to simultaneously shape and laminate the two layers. It is to be noted that during the laminating process, the two layers should not be under significant compacting pressure to avoid appreciable compaction of the nonwoven fiber web.

As yet another alternative embodiment of the present invention, the laminate of the present invention can be formed by directly extruding a layer of a thermoplastic polymer onto the lofty nonwoven layer, thereby eliminating the separate barrier layer forming step and the laminating step. Thermoplastic polymers suitable this process are selected from the above-described thermoplastic polymers for the liquid-barrier layer.

The present thermoformable liquid-barrier laminate exhibits high resiliency and flexibility that allow the thermoformed articles produced therefrom in accordance with the present invention to conform to distorting movements and pressures applied on the articles and allow the articles to resiliently return to the thermoformed shape when the movements and pressures are removed. Particularly useful thermoformable liquid-barrier laminates of the present invention have a Gurley bending stiffness between about 15 and about 20,000, more particularly between about 50 and 10,000, most particularly between about 150 and 5,000, as measured in accordance with the TAPPI T543PM-84 testing procedure.

In accordance with the present invention, the present laminate is thermoformed in a thermoforming process that does not apply significant compacting pressures during the thermoforming process and does not allow large areas of the component layers of the laminate to touch a heated or high temperature surface such that significant compaction and thermal fusion and distortion of the laminate layers are avoided. Alternatively stated, the thermoforming process does not significantly alter the lofty, soft and cloth-like properties of the nonwoven web layer and the barrier properties and dimensional stability of the liquid-barrier layer. Particularly desirable thermoforming processes for the present invention produce thermoformed articles having a density-over-area ratio between about 1 and about 2.5, more desirably between about 1.05 and about 1.8, most desirably between about 1.1 and about 1.5. The term "density-over-area ratio" as used herein is defined as $(D_i/D_o)/(A_i/A_o)$, wherein $D_i$ is the average density of the thermoformed article, $D_o$ is the average density of the substrate web, $A_i$ is the total surface area of the thermoformed article and $A_o$ is the total surface area of the substrate web that is placed over the opening of the mold, i.e., the surface area affected by the thermoforming process. Suitable thermoforming processes for the present invention, which do not adversely affect the lofty, cloth-like texture and barrier properties of the barrier laminate, have the steps of heating the laminate to a temperature that is sufficiently high enough to at least soften the adhesive component of the laminate but below the melting temperature of the structural component, shaping the heated laminate against an unheated mold, and cooling the shaped laminate.

Heating processes suitable for the present laminate need to heat the laminate, without applying compacting pressure, to a temperature that is high enough to at least soften the adhesive component of the nonwoven layer but below the melting point of the structural component. These processes may utilize a heating medium such as steam, heated air or gas, radiation, e.g., infrared light, and the like. A particularly desirable process, which is known as the heated-air heating process, applies a flow of pressurized heated gas or air onto the nonwoven side of the laminate to evenly and rapidly distribute the heat throughout the nonwoven layer.

Although, as stated above, adhesively bonded monocomponent and conjugate fiber webs and autogenously bonded conjugate fiber webs can be utilized to produce the thermoformed articles of the present invention, hereinafter the invention is described with a laminate containing a conjugate fiber nonwoven layer and a thin polymeric film layer for illustration purposes. It is to be noted that the processes and description for melting and bonding the adhesive component polymer of conjugate fibers are analogously applicable to the processes and description for the external hot-melt adhesive that may be employed to bond the structural fiber component of the nonwoven web.

A suitable thermoforming process for the present invention is the mold-assist mold thermoforming process. A thermoformable laminate is heated to render the laminate, more specifically the nonwoven layer, pliable using any known heating process that evenly heats the laminate. The heated, pliable laminate is placed over a male or female mold and assisted by a reciprocating assist mold that assists shaping the pliable laminate. Then the shaped laminate is cooled to allow the adhesive component of the laminate to set, permanently fixing the molded shape. The assist mold is designed to have a minimal surface contact with the laminate and is placed on the opposite side of the laminate away from the mold. The assist mold guides the pliable laminate to conform to the peripheral contour of the mold. The molds of the present invention are not heated and, desirably, are cooler than the temperature of the heated laminate to act as a heat sink, shortening the duration of the cooling cycle of the thermoformed article. In addition, particularly desirable thermoforming processes for the present invention essentially allow only the liquid-barrier layer to contact the mold surface, avoiding compaction of the nonwoven fiber web layer.

The molding process can be further assisted by pneumatic forces, such as vacuum or forced-air, that is applied on the pliable laminate to assist the shaping process. It is to be noted that the pressure of the pneumatic assist should not be too high as to appreciably compress the component fibers of the laminate. In addition, the mold and the assist mold should not form a tight fit when the molds are mated, avoiding compaction of the laminate during the thermoforming process. It is highly desirable that when the mold and assist mold are mated or closed, the molds form a clearance of about the thickness of the laminate.

Figure 3:
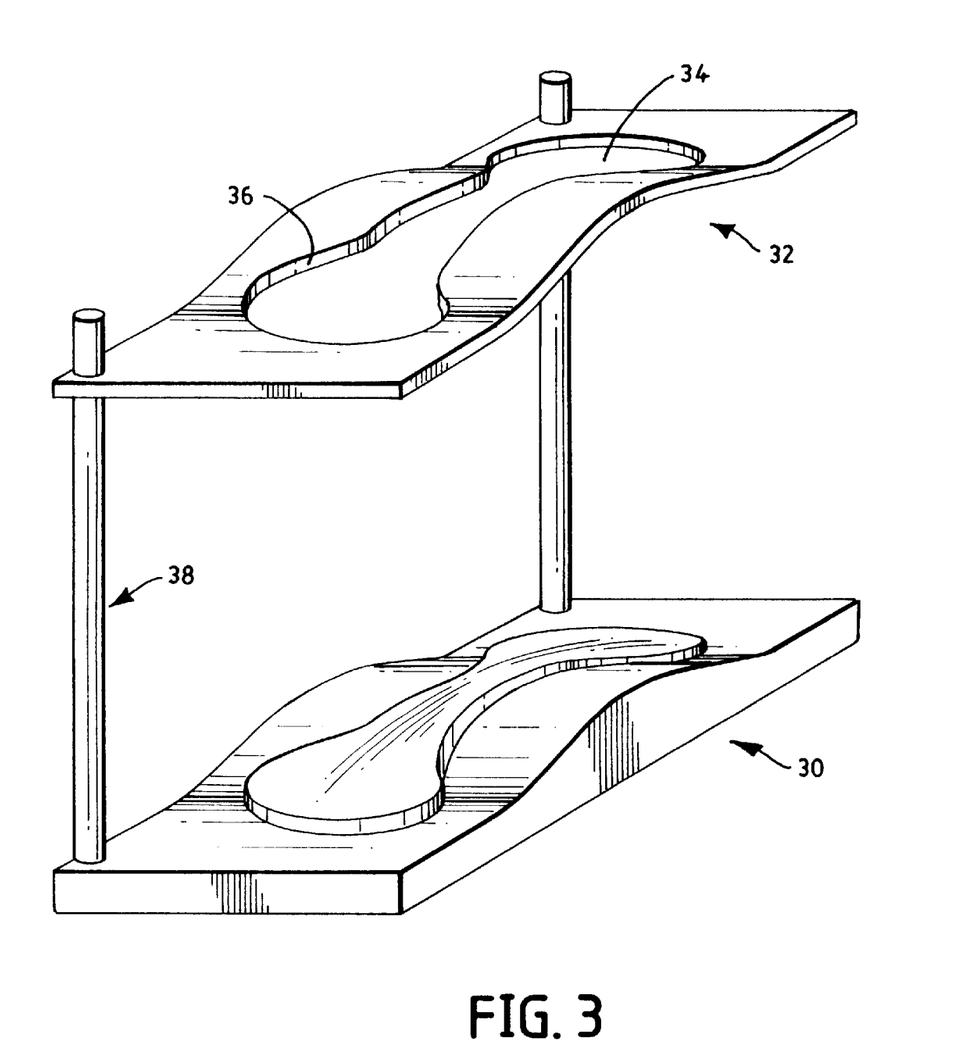
FIG. 3 illustrates a mold unit that is suitable for thermoforming the barrier laminate.

FIG. 3 illustrates a suitable male mold 30 and an assist mold 32. The assist mold 32 is a hollow structure which has an opening 34 that corresponds to the shape of the base section of the male mold 30. The opening 34 is slightly larger than the base section of the mold 30 such that the thermoformed web is not appreciably or significantly compacted when the molds are mated. It is to be noted that the assist mold is designed to contact the pliable web only at a limited area, e.g., at the edge 36 of the assist mold. Optionally, if the shape of the mold contains complicated or inwardly-shaped contours, the opening of the assist mold may be equipped with a lining of an extension of a flexible material, such as a high temperature rubber or thermoplastic elastomer, to facilitate the assist mold in flexibly applying relatively even pressures on the pliable web throughout the contacting area. Optionally, the male mold 30 and the assist mold 32 can be guided by stabilizer-guiding rods 38 that ensure proper engagement of the two molds, and the mold 30 may further contain slits or perforation on its surface to supply a flow of air or vacuum to assist the thermoforming process.

The unheated mold tends to act as a heat sink, cooling the preheated web as the web comes in contact with the mold and pliably conform to the outside contour of the mold. Unlike thermoforming processes using a heated mold, the present thermoforming process does not melt fuse the web fibers that contact the mold surface, avoiding melt-fusion of the web fibers at the surface and retaining the soft, cloth-like textures. Additionally, the unheated mold alleviates the uncontrollable shrinkage problem that generally accompanies attempts that thermoform thin films on a heated mold. Moreover, articles molded with the present unheated mold thermoforming process need not be held in the mold for an extended duration since the mold, acting as a heat sink, rapidly cools the preheated, thermoformed web to retain its molded shape. The shaped laminate may be additionally cooled with a flow of air while the laminate is in or on the mold to accelerate the cooling process. The shaped article can be completely cooled in the mold or removed from the mold after the article becomes semi-rigid and is able to retain its shape.

Molds suitable for the present invention can be fabricated from metals, wood, plaster, plastics and the like in accordance with mold forming procedures well known in the art. Desirably, the molds are fabricated from a metal having a high thermal conductivity. Further, since the present molding process does not apply high molding and compacting pressures, suitable molds can be fabricated from rigid metal or plastic wire mesh structures. Optionally, the molds can be equipped with a cooling, compressed-air and/or vacuum applying means to facilitate the molding process. In addition, the surface of the mold may contain a pattern of raised regions such that the thermoformed articles produced from the mold contain a pattern corresponding to the mold surface pattern.

Although the present invention is illustrated with a sanitary napkin shell which is thermoformed from a two-layer laminate and has its nonwoven layer exposed to the outside, the laminate and thus the thermoformed articles of the present invention may have more than two layers and/or may have its nonwoven layer placed inside the thermoformed article. For example, a three-layer laminate having a nonwoven layer, a liquid-barrier layer and a nonwoven layer can be produced and thermoformed in accordance with the disclosure of the present invention. Having a nonwoven layer inside the thermoformed article is highly useful, e.g., in personal care articles. For example, the lofty and thus porous structure of the nonwoven layer is highly useful for handling liquids applied thereon. The lofty, porous structure provides interstices that are highly suitable for holding, intaking and/or distributing liquid. In addition, the nonwoven layer can be treated to carry functional or filler materials. The lofty nonwoven layer of the present invention, which contains evenly distributed interfiber bonds, has an interfiber structure that is highly amenable for entrapping particulates of functional or filler materials, such as, wood pulp, superabsorbent particles, odor-absorbent particles, carbon particles, antimicrobial particles and the like.

The barrier nonwoven laminate of the present invention is particularly useful for thermoforming the skin-contacting outerlayer of personal-care articles, such as diaper parts, sanitary napkin shells, incontinent adult care product parts and the like. Such thermoformed articles not only provide excellent resilient compressibility and barrier properties but also exhibit cloth-like textures, making the articles highly functional as well as highly comfortable for the users. Particularly, for personal-care articles, the resiliency and texture of the thermoformed articles allow the articles to conform to bodily movements of the users while providing comfortable cloth-like textures and resiliency to retain the thermoformed shape.

The present invention is not limited to the thermoformed articles for personal-care products although the invention is illustrated above in reference to personal-care products. The present thermoformable laminate can be utilized in various applications that benefits from the cloth-like appearance and easy thermoformability as well as liquid barrier properties. Illustrative of such applications include cloth linings, scrubbing pads, automotive interior parts and the like.

The following examples are provided for illustration purposes and the invention is not limited thereto.

EXAMPLES

Example 1

A three-dimensional shell of an hourglass shaped sanitary napkin was prepared from a laminate of a spunbond nonwoven web and a film. A 3 osy spunbond bicomponent fiber web was produced in accordance with aforementioned U.S. patent application Ser. No. 08/933,444. A linear low density polyethylene (LLDPE), Aspun 6811A, which is available from Dow Chemical, was blended with 2 wt % of a $TiO_2$ concentrate containing 50 wt % of $TiO_2$ and 50 wt % of a polypropylene, and the mixture was fed into a first single screw extruder. A polypropylene, PD3445, which is available from Exxon, was blended with 2 wt % of the above-described $TiO_2$ concentrate, and the mixture was fed into a second single screw extruder. The extruded polymers were spun into round bicomponent fibers having a side-by-side configuration and a 1:1 weight ratio of the two component polymers using a bicomponent spinning die, which had a 0.6 mm spinhole diameter and a 6:1 L/D ratio. The melt temperatures of the polymers fed into the spinning die were kept at 415° F., and the spinhole throughput rate was 0.75 gram/hole/minute. The bicomponent fibers exiting the spinning die were quenched by a flow of air having a flow rate of 45 SCFM/inch spinneret width and a temperature of 65° F. The quenching air was applied about 5 inches below the spinneret, and the quenched fibers were drawn in an aspirating unit of the type which is described in U.S. Pat. No. 3,802,817 to Matsuki et al. The aspirator was equipped with a temperature controlled aspirating air source, and the feed air temperature was kept at about 350° F. The quenched fibers were drawn with the heated feed air to attain a 4 denier thickness. Then, the drawn fibers were deposited onto a foraminous forming surface with the assist of a vacuum flow to form an unbonded fiber web. The unbonded fiber webs were bonded by passing the web through a through-air bonder which is equipped with a heated air source. The heated air velocity and the temperature of the heated air was 200 feet/minute and 262° F., respectively. The residence time of the web in the hood was about 1 second. The resulting bonded web had a thickness of 0.13 inches and a density of 0.0309 g/cm$^3$.

A 2 mil polypropylene film, XBPP-15.2, was obtained from CT Industries. The film was sprayed with a hot-melt adhesive, National Starch 34-5541, and laminated without applying significant compacting pressure on the nonwoven web. The thickness of the laminate was about 0.15 inches. The laminate was tested for the Gurley bending stiffness in accordance with TAPPI T543PM-84. The result is shown in Table 1.

The laminate was thermoformed into a shell by placing it in an oven which applied flows of heated air at 325° F. for 6.5 seconds, and then feeding the heated laminate in an hourglass shaped mold, which is illustrated in FIG. 3 and had a length of about 9.25 inches and an average depth of about 0.88 inches. The film side of the laminate was placed next to the male mold and the nonwoven fiber web side was placed to contact the assist female mold. The assist mold was lined with a flexible polyurethane extension of about ¾ of an inch at the two edges of the narrow middle section to accommodate the narrowing contour of the male mold at that section. The male and assist molds were closed and remained in position for 10 seconds, while the molds were cooled with a fan, before the thermoformed article is removed from the mold. The closed molds formed a gap approximately equal to the thickness of the laminate, except for the middle section where the flexible extensions snugly compressed the laminate to the male mold.

The resulting thermoformed shell had an average thickness of about 0.08 inches and largely retained the soft, cloth-like texture of the substrate laminate. Even the wall of the middle section of the shell, which was expected to be highly stretched during the thermoforming process, essentially retained the soft, cloth-like texture. The thermoformed article had a high resiliency that allowed the article to return to its thermoformed shape when it is subjected to different directional deforming pressures, and the density-over-area ratio of the thermoformed article was about 1.12.

Comparative Example 1

The barrier laminate of Example 1 was prepared and heated in accordance with the procedure outlined in Example 1 and then was thermoformed in a female mold that had the inverse shape of the male mold of Example 1. The female mold, which was fabricated from aluminum, contained a multitude of bored vacuum holes, and the vacuum holes were connected to a vacuum apparatus such that the apparatus can apply a drawing flow of air toward the female mold. The heated laminate was placed on the mold with its nonwoven layer contacting the mold surface. Then immediately the vacuum apparatus was turned on to forcefully draw the laminate toward the mold surface, shaping and compacting the laminate. The resulted thermoformed shell was highly compacted and had an average thickness of about 0.015 inches, and the nonwoven layer exhibited a film-like texture. The thermoformed shell had a density-over-area ratio of about 3. The shell was stiff, and the edges of the shell was uncomfortably sharp, making this compressed shell unfit for skin-contacting uses.

Unlike the shell of Comparative Example 1, the thermoformed article that is produced in accordance with the present invention, i.e., the shell of Example 1, is a resiliently compressible article that exhibits pleasing and comfortable textural properties.

Control 1

A 4 mil polypropylene film, which is available from CT Industries, was tested for the Gurley bending stiffness. The result is shown in Table 1.

Controls 2–3

⅟₁₆ and ⅟₃₂ of an inch thick flexible polyethylene foam sheets, Volara™ E-O grade, which are available from Voltek, Corp., Massachusetts. These foam sheets are the type of polyethylene sheets that are commercially used to produce the shell of incontinence-pads. The foam sheets were tested for the Gurley bending stiffness. The results are shown in Table 1.

TABLE 1

| Example | Stiffness |
| --- | --- |
| Example 1 | 166 |
| Control 1 | 13 |
| Control 2 | 270 |
| Control 3 | 142 |

The results demonstrate that the cloth-like laminate of the present invention exhibits a desirable bending property that is similar to flexible polyethylene foam sheets, while providing a comfortable, cloth-like texture.

What is claimed is:

1. A three-dimensional thermoformed shaped article comprising a barrier laminate having a liquid barrier layer and a lofty crimped-fiber nonwoven web layer, said barrier laminate having a maximum thickness, a cloth-like texture and liquid barrier property, wherein:

said liquid barrier layer is selected from films, microfiber nonwoven webs and laminates thereof, said lofty crimped fiber nonwoven web layer has substantially uniformly distributed interfiber bonds and comprises multicomponent fibers having a structural component and a heat-activatable adhesive component, wherein said adhesive component comprises a thermoplastic polymer having a melting point which is lower than the melting point of said structural component, and said barrier laminate is thermoformed into a permanent, self-sustaining three-dimensional shape which is resiliently reversibly deformable and further wherein the three-dimensional shape formed by said thermoformed barrier laminate has dimensions in each of the x, y and z directions greater than the maximum thickness of said barrier laminate.

2. The thermoformed article of claim 1 wherein said structural component comprises a fiber-forming thermoplastic polymer selected from polyolefins, polyamides, polyesters, polycarbonates, polystyrenes, thermoplastic elastomers, fluoropolymers, vinyl polymers, and blends and copolymers thereof.

3. The thermoformed article of claim 1 wherein said structural component comprises polypropylene and said adhesive component comprises polyethylene.

4. The thermoformed article of claim 1 wherein said adhesive and structural components of said nonwoven web layer are present in the form of a conjugate fiber.

5. The thermoformed article of claim 4 wherein said conjugate fiber comprises a side-by-side bicomponent fiber comprising polypropylene and high density polyethylene.

6. The thermoformed article of claim 4 wherein said conjugate fiber comprises a side-by-side bicomponent fiber comprising polypropylene and linear low density polyethylene.

7. The thermoformed article of claim 1 wherein said barrier layer comprises a thermoplastic polymer selected from polyethylene, polypropylene and blends thereof.

8. The thermoformed article of claim 1 is a shell for an absorbent article.

9. The thermoformed article of claim 1 wherein said article has an inside surface and outside surface, and said nonwoven web layer forms said outside surface.

10. The thermoformed article of claim 1 wherein said article has an inside surface and outside surface, and said nonwoven web layer forms said inside surface.

11. The thermoformed article of claim 10 wherein said nonwoven web layer contains functional particulates.

12. The three-dimensional article of claim 1 wherein said barrier layer comprises a film.

13. The three-dimensional article of claim 12 wherein said crimped fiber nonwoven web layer comprises conjugate spunbond fibers.

14. The three-dimensional article of claim 13 wherein said film comprises a breathable microporous film.

15. The three-dimensional article of claim 13 wherein said film and the adhesive component of said crimped fiber nonwoven comprise the same polymer.

16. A three-dimensional thermoformed article of claim 1 made by the process comprising:

forming said barrier laminate; and thereafter thermoforming said barrier laminate into said three-dimensional shape wherein said thermoformed article has a density-over-area ratio between about 1 and about 1.5.

17. A thermoformed article of claim 16 wherein said formed barrier laminate has a gurley bending stiffness of between about 15 and 20,000.

18. The thermoformed article of claim 1 wherein said three-dimensional shape comprises the shape of a personal care article.

19. The thermoformed article of claim 18 wherein said three-dimensional shape comprises a shell having an hourglass configuration.

20. The thermoformed article of claim 1 wherein said self-sustaining three-dimensional shape comprises a shell.

* * * * *